US005806529A

United States Patent [19]
Reisner et al.

[11] Patent Number: 5,806,529
[45] Date of Patent: Sep. 15, 1998

[54] BONE MARROW TRANSPLANTATION

[75] Inventors: Yair Reisner, Old Jaffa, Israel; Massimo Martelli, Perugia, Italy

[73] Assignee: Yeda Research and Development Co. Ltd., Israel

[21] Appl. No.: 333,393

[22] Filed: Nov. 2, 1994

[30] Foreign Application Priority Data

Nov. 3, 1993 [IL] Israel ......................................... 107483

[51] Int. Cl.$^6$ ................................................. A61B 19/00
[52] U.S. Cl. ............................................................. 128/898
[58] Field of Search ....................................... 128/897–98

[56] References Cited

PUBLICATIONS

Caspar, et al., "Effective Stimulation of Donors for Granulocyte Transfusions With Recombinant Methionyl Granulocyte Colonystimulating Factor", *Blood*, 81:2866–71 (1993).
Cordell et al., "Immunoenzyme Labeling of Monoclonal Antibodies Using Immune Complexes of Alkaline Phosphatase and Monoclonal Anti–Alkaline Phosphatase (APAAP complexes)", *J. Histochem. Cytochem.*, 32:219 (1984).
Gale and Reisner, "Graft Rejection and Graft–Versus–Host–Disease: Mirror Images", *Lancet* 1:1468 (1986).
Gianni et al., "Durable and Complete Hematopoietic Reconstitution After Autografting of rhGM–CSF Exposed Peripheral Blood Progenitor Cells", *Bone Marrow Transplant* 6:143 (1990).
Glucksberg et al., "Clinical Manifestations of Graft–Versus–Host Disease in Human Recipients of Marrow From HLA–Matched Sibling Donors", *Transplantation*, 18:295 (1974).
Lapidot et al., "Enhancement by Dimethyl Myleran of Donor Type Chimerism in Murine Recipients of Bone Marrow Allografts", *Blood* 73:2025.
Matsunaga et al., "Recombinant Human Granulocyte Colony–Stimulating Factor Can Mobilize Sufficient Amounts of Peripheral Blood Stem Cells in Healthy Volunteers for Allogeneic Transplantation", *Bone Marrow Transplant*, 11:103 (1993).
Molineux et al., "Transplantation Potential of Peripheral Blood Stem Cells Induced by Granulocyte Colony–Stimulating Factor", *Blood*, 76:2153 (1990).
O'Reilly et al., "Transplantation of Marrow Depleted of T–Cells by Soybean Lectin Agglutination and E–Rosette Depletion: Major Histocompatibility Complex–Related Graft Resistance in Leukemia Transplant Recipients", *Transplant Proc.*, 17:455 (1985).
O'Reilly et al., "Allogeneic Transplants Depleted of T–Cells by Soybean Lectin Agglutination and E–Rosette Depletion", *Bone Marrow Transplant* 3:(1):3 (1988).
Reisner et al., "Hemopoietic Stem Cell Transplantation Using Mouse Bone–Marrow and Spleen Cells Fractionated by Lectins", *Proc. Natl. Acad. Sci. USA*, 75:2933 (1978).

Reisner et al., "Transplantation for Acute Leukemia With HLA–A and B Nonidentical Parental Marrow Cells Fractionated With Soybean Agglutinin and Sheep Red Blood Cells", *Lancet II*, 327 (1981).
Reisner et al., "Allogeneic Bone Marrow Transplantation in Mouse, Monkey and Man Using Lectin–Separated Grafts", *Tolerance in Bone Marrow and Organ Transplantation*, Elsevier, Slavin, S. (ed.) p. 293 (1984).
Reisner et al., "A Shorter Procedure for Preparation of E–Rosette–Depleted Bone Marrow for Transplantation", *Transplantation*, 42:312 (1986).
Russel et al., "Peripheral Blood Stem as an Alternative to Marrow for Allogeneic Transplantation", *Lancet* 341: 1482 (1993).
Terenzi et al., "Enhancement of T–Cell Depleted Bone Marrow Allografts in Mice by Thiotepa", *Transplantation* 50:717 (1990).
Vallera and Blazer, "T–Cell Depletion for Graft–Versus–Host Disease (GVHD) Prophylaxis: A Perspective on Engraftment in Mice and Humans" *Transplantation* 47:751 (1989).
Velardi et al., "Acquisition of Immunoglobulin Isotype Diversity After Bone Marrow Transplantation in Adults. A Recapitulation of Normal B–cell Ontogeny", *J. Immunol.* 141:815 (1988a).
Velardi et al., "Imbalance Within Peripheral Blood T–Helper (CD4+) and T–suppressor (CD8+) Cell Populations in the Reconstitution Phase After Human Bone Marrow Transplantation", *Blood* 71:1196 (1988b).
Velardi et al., "Cytolytic Functions of Clonable T–Cells After Human Bone Marrow Transplantation", *Blood* 75:1364 (1990).
Weaver et al., "Synergeneic Transplantation With Peripheral Blood Mononuclear Cells Collected After the Administration of Recombinant Human Granulocyte Colon–Stimulating Factor", *Blood* 82:1981.
Yam et al., "Use of DNA Restriction Fragment Length Polymorphisms to Document Marrow Engraftment and Mixed Hematopoietic Chimerism Following Bone Marrow Transplantation", *Transplantation* 43:399 (1987).

(List continued on next page.)

*Primary Examiner*—John P. Lacyk
*Attorney, Agent, or Firm*—Pennie & Edmonds

[57] ABSTRACT

The present invention provides a method for bone marrow transplantation from an HLA-nonmatched donor to a patient which comprises conditioning the patient under a suitable regimen followed by transplant of a very large dose of stem cells which is at least about 3-fold greater than the conventional doses used in T cell-depleted bone marrow transplantation. The patient is conditioned under lethal or supralethal conditions for the treatment of malignant or non-malignant diseases, or under sublethal conditions for the treatment of non-malignant diseases. The transplant may consist of T cell-depleted bone marrow stem cells and T cell-depleted stem cell-enriched peripheral blood cells from the HLA-nonmatched donor. preferably a relative of the patient, which donor was previously treated with a drug, e.g. a cytokine such as granulocyte colony-stimulating factor (G-CSF).

32 Claims, 2 Drawing Sheets

PUBLICATIONS

Zinzani et al., 1993, "Granulocyte colony stimulating factor G–CSF as adjunct therapy in relapsed–resistant high–grade non–Hodgkin's lymphoma ", Haematologica 78(1):40–43.

Reisner and Gan, 1985, "Differential binding of soybean agglutinin to human neuroblastoma cell lines: Potential application to autologous bone marrow transplantation", Cancer Research 45(9):4026–4031.

Reisner, "Engraftment of T–cell–depleted Bone Marrow in Murine Models for Allogeneic Bone Marrow Transplantation", In *Bone Marrow Transplantation*, Kluwer Academic Publishers, R. Champlin (ed.), p. 9 (1990).

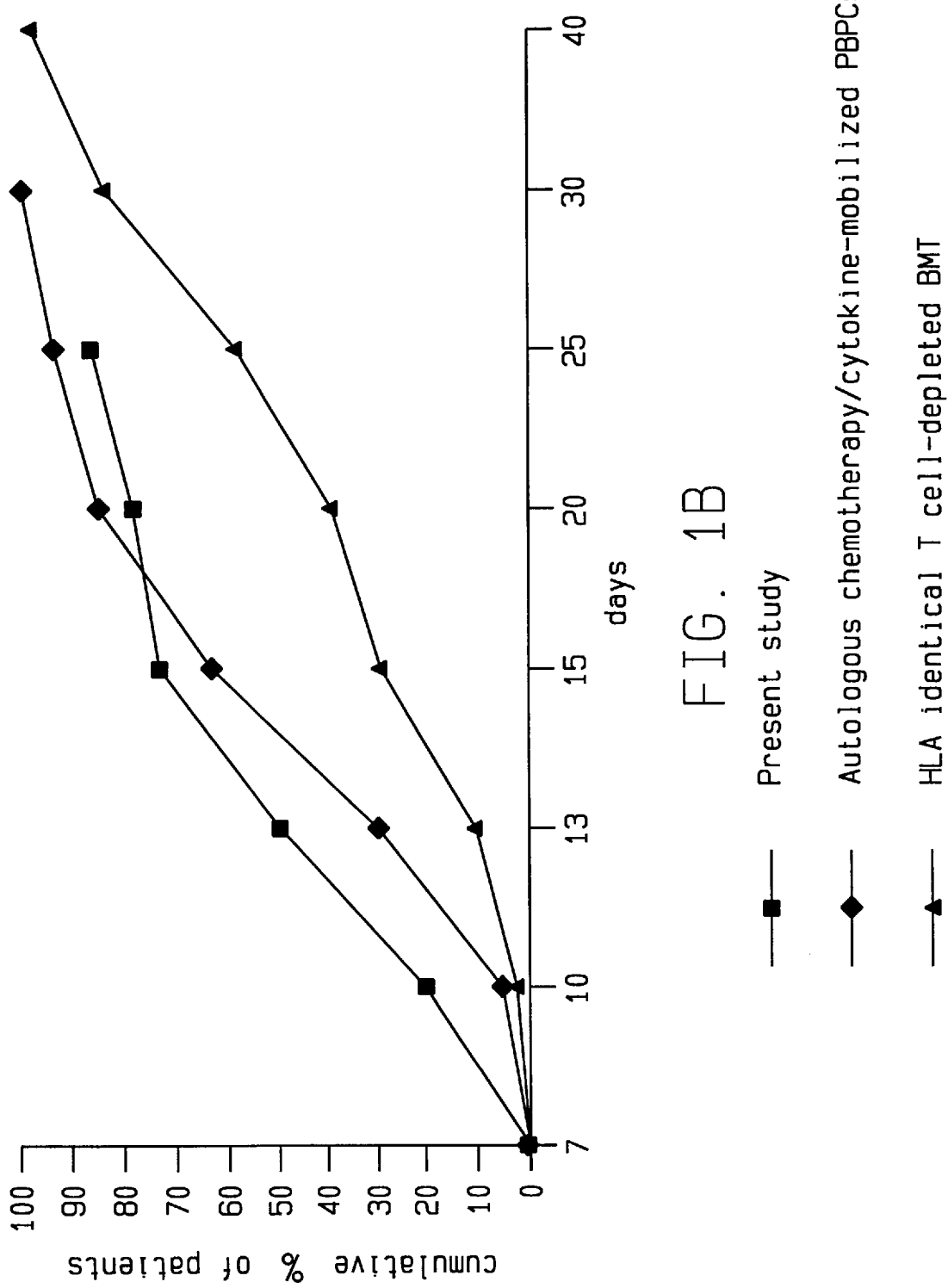

BONE MARROW TRANSPLANTATION

FIELD AND BACKGROUND OF THE INVENTION

The present invention relates to bone marrow transplantation in humans, particularly from HLA-nonmatched donors.

Bone marrow transplantation (BMT) is being increasingly used in humans. In genetically identical twins there are no immunological barriers to BMT, but in other circumstances genetic disparities result in immune-related complications, including graft rejection and graft-versus-host disease (GVHD) (Gale and Reisner, 1986).

GVHD can be prevented by using T-cell-depleted bone marrow. Since 1980, we and others have successfully used mismatched T-cell-depleted marrow for the treatment of children with severe combined immune deficiency (SCID) (for reviews, see O'Reilly et al., 1989; Reisner et al., 1984; Reisner, 1990). The newly formed donor-type T cells in these patients are tolerant of the host and do not induce GVHD. Based on these promising results, the use of T-cell-depleted bone marrow was extended to the treatment of leukemia patients for whom matched sibling donors were not available and to those individuals who had matched sibling donors but were nevertheless at high risk for GVHD.

However, the experience with leukemia patients was disappointing, due to a high rate of graft rejection or graft failure. In recipients of HLA-identical T-cell-depleted bone marrow, the incidence of graft rejection is about 10–15%, whereas in recipients of HLA-nonidentical T-cell-depleted marrow, the rate of rejection is about 50% (O'Reilly et al., 1985).

Bone marrow allograft rejection has been documented extensively in different animal models (Reisner, 1990; Vallera and Blazer, 1989). In the mouse it can be overcome simply by increasing the marrow inoculum. We and others have been able to produce long-term immunologically vigorous chimera with a high rate of success (Reisner, 1990). A key question, therefore, is whether the differences between T-cell-depleted transplants in mouse and man are simply due to technical discrepancies, such as the low number of pluripotent stem cells in the human bone marrow aspirate (which is limited to the iliac crest and is highly contaminated with peripheral blood), or whether they reflect the great disparity between outbred humans as opposed to inbred mice. Recent studies carried out in our laboratory have illustrated the quantitative basis of bone marrow allograft rejection and strongly indicate that the former possibility is more likely to be true. Thus, in the mouse model, reduction of the hematological parameters typical for marrow rejection was positively correlated with several parameters reflecting the residual immunity remaining after the conditioning with lethal irradiation, and inversely correlated with the marrow inoculum size. In particular, it was demonstrated that, even in the most stringent murine models of bone marrow allograft rejection, this complexed reaction can be overcome if a sufficiently large marrow transplant is used.

More recently, advances made in the area of autologous BMT have shown that, in cancer patients receiving such transplants, treatment with granulocyte colony-stimulating factor (G-CSF) or other cytokines, such as granulocyte macrophage colony-stimulating factor (GM-CSF) or interleukin-3 (IL-3), leads not only to elevated levels of neutrophils in the peripheral blood, but also to mobilization of pluripotential stem cells from the marrow to the blood. Thus, following induction with G-CSF, it became possible to collect by leukapheresis large numbers of stem cells (Caspar et al., 1993).

Among the diseases that can be treated with success by bone marrow transplantation, are more than 20 otherwise fatal diseases that include the six or seven genetically different forms of SCID, various forms of congenital or genetically determined hematopoietic abnormalities, combinations of these two, certain anemias, osteopetrosis, a variety of high risk leukemias and several forms of severe life-threatening aplastic anemia. These diseases include SCID autosomal recessive with and without B cells (no ADA deficiency); SCID X-linked recessive without B cells; SCID autosomal recessive with ADA deficiency; Wiskott-Aldrich syndrome; Blackfan-Diamond syndrome; Fanconi anemia; severe neutrophil dysfunction; chronic granulomatous disease of childhood; severe (Kostman-type) agranulocytosis; immunodeficiency and neutropenia of cartilage-hair hypoplasia; infantile and late onset osteopetrosis; aplastic anemia-toxic chemical, idiopathic, immunological, and genetic (non-Fanconi); acute myeloid leukemia; chronic myeloid leukemia; Burkitt lymphoma, and recurrent acute lymphatic leukemia. Other diseases that have been treated recently with BMT include metabolic storage diseases such as Gaucher's disease, hemoglobinophaties such as thalassemia, and even some solid tumors such as neuroblastoma. In addition, BMT can be carried out before transplantation of an organ, e.g. kidney, from a same donor to a patient.

More general application of allogeneic BMT for the treatment of patients with hematologic malignancies or other disorders is restricted by the availability of suitable donors. Less than 30% of patients who might benefit from transplant have genotypically HLA-identical siblings and only 3–5% have an one HLA-locus mismatched relative. In contrast, nearly all patients have an HLA-haploidentical relative (parent, child, sibling) who could serve as a donor. To date, transplantation of unmodified bone marrow from HLA-haploidentical two or three loci incompatible donors has been associated with unsuccessful outcome due to the high incidence (80%) of severe GVHD. The risk of graft failure may be 20% or higher. Extensive T cell-depletion of mismatched donor marrow can be used to effectively prevent GVHD, but the undesirable consequence of such transplants has been an increase in the incidence of graft failure to as high as 50% (O'Reilly, 1985 and 1988).

In view of the expanded approach to treatment of many severe diseases with BMT, a method for achieving high rates of engraftment of bone marrow cells from HLA-nonmatched donors, with low incidences of graft rejection and GVHD, would be highly desirable.

SUMMARY OF THE INVENTION

It is an object of the present invention to provide a method for treatment of a patient by bone marrow transplantation which comprises transplanting to said patient, after conditioning under a suitable regimen, a very large dose of stem cells, preferably a dose at least about 3-fold greater than the doses usually used in conventional T-cell-depleted bone marrow transplantation, from an LA-nonmatched donor.

The method of the invention is accomplished, for example, by transplanting to the host patient T-cell-depleted bone marrow cells and T-cell-depleted stem cell-enriched peripheral blood cells from an HLA-nonmatched donor, such as an HLA haploidentical "three loci" incompatible family member, said stem cells of the peripheral blood being mobilized by treatment of the donor with a suitable cytokine, e.g G-CSF.

BRIEF DESCRIPTION OF THE FIGURES

FIGS. 1A–B depict curves representing cumulative proportions of patients reaching 500 (1A) and 1000 neutrophils (1B).

DETAILED DESCRIPTION OF THE INVENTION

Figure 1A:
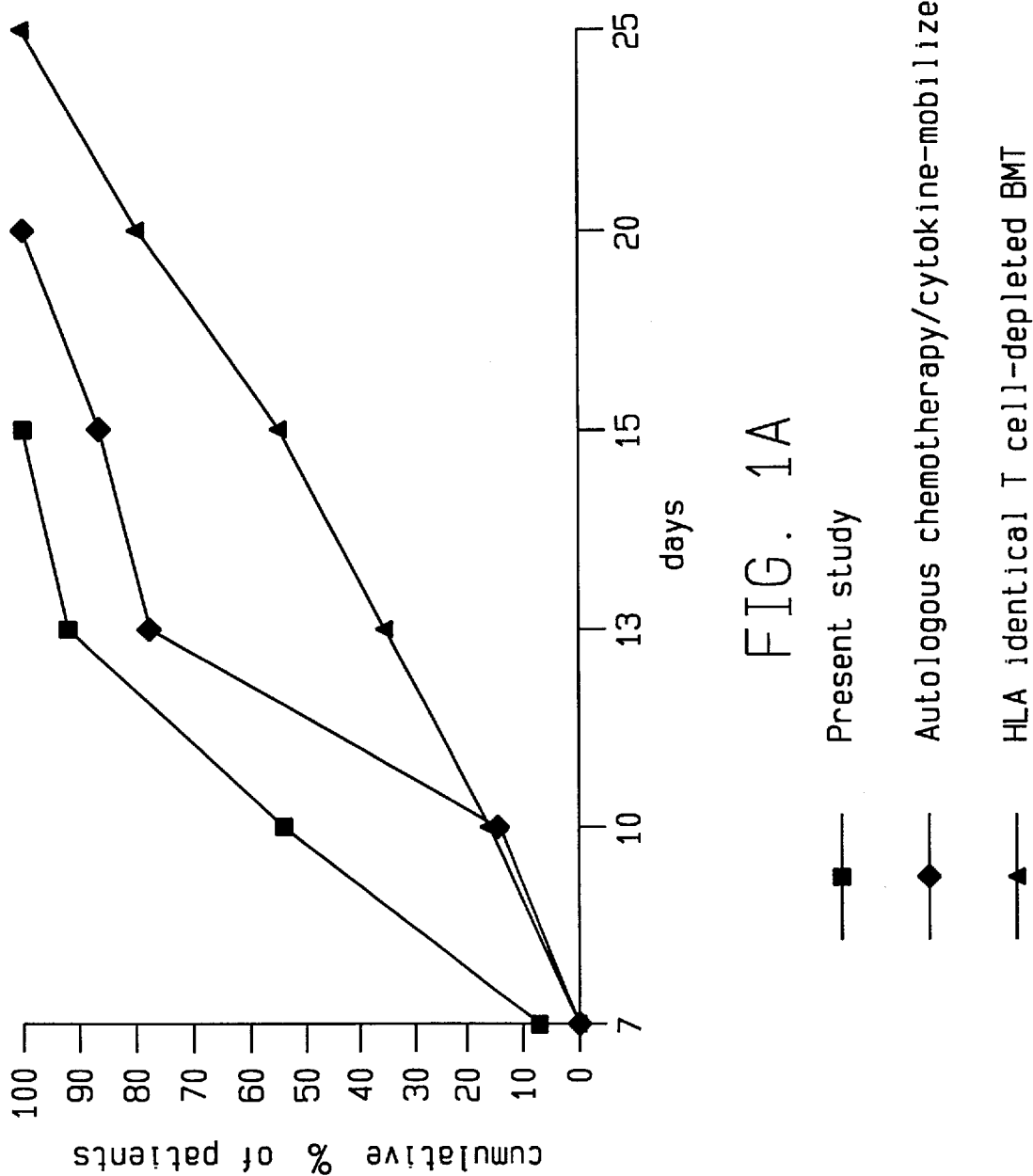

Graft failure is presumably a result of the immunological rejection of donor hemopoietic cells by the host residual immune system, but it could also be mediated by other mechanisms, including competition between donor and residual host stem cells for the limited available niches in the bone marrow stroma, as well as the availability of facilitating cells in the donor inoculum. In the mouse model, the immunological rejection of T cell-depleted histoincompatible BMT can be overcome by increasing radiation or by adding selective measures with minimal toxicity, such as splenic irradiation or in vivo treatment with anti-T monoclonal antibodies, to the conditioning regimen. Stem cell competition can be manipulated in favour of donor type cells by increasing the size of the T-cell depleted bone marrow inoculum (Reisner, 1978) or by adding myeloablative drugs (busulphan, thiotepa) to the radiation therapy (Lapidot et al., 1988; Terenzi et al., 1990).

The means of overcoming graft failure elucidated in the experimental model can be applied in the clinical setting by combining approaches which increase both the conditioning of the host and the size of the stem cell inoculum.

To this end, we designed a conditioning regimen which added anti-thymocyte globulin (ATG) and thiotepa, a powerful myeloablative agent, to cyclophosphamide and total body irradiation (TBI) in a single fraction at a fast dose rate, to enhance both immunosuppression and myeloablation. It has recenlty been demonstrated that the administration of recombinant human granulocyte colony-stimulating factor (rhG-CSF) or recombinant human granulocyte-macrophage colony-stimulating factor (rhGM-CSF) can mobilize a sufficient number of peripheral blood progenitor cells (PBPC) to permit the collection of a transplant inoculum (Matsunaga et al., 1993). Infusion of these cytokine-mobilized cells has resulted in rapid marrow recovery and sustained hematopoiesis in autologous (Gianni et al., 1990) and syngeneic transplants (Weaver et al., 1993). Two cases of allogeneic PBPC transplant have also been reported (Russel et al., 1993). Moreover, studies on PBPC transplants in animals have indicated that PBPCs can provide long-term multilineage hematopoiesis (Molineux et al., 1990).

Therefore, we attempted to increase the overall number of colony forming units-granulocyte/macrophage (CFU-GM) infused into the recipients by an order of magnitude by adding to the T cell-depleted bone marrow, peripheral blood progenitor cells obtained from the donor after the administration of rhG-CSF. These cells were subjected to the same T cell-depletion procedure. No post-grafting immunosuppressive treatment was given.

According to the invention the host patient is conditioned prior to the transplantation of stem cells. Conditioning may be carried out under sublethal, lethal or supralethal conditions, for example by total body irradiation (TBI) and/or by treatment with myeloablative and immunosuppressive agents. According to standard protocols, a lethal dose of irradiation is within the range of 7–9,5 Gy TBI, a sublethal dose is within the range of 3–7 Gy TBI and a supralethal dose is within the range of 9,5–16 Gy TBI.

Several protocols are known for conditioning of the host patient with a myeloablative and an immunosuppressive agent without TBI. As an example, busulphan is administered from day −8 to day −5 at a daily dose of 1–2 mg/kg (sublethal), 2–5 mg/kg (lethal) or >5 mg/kg (supralethal), followed by 50 mg/kg cyclophosphamide daily in the three regimens from day −4 to day −1.

Usually, lethal and supralethal conditioning are used to treat patients having malignant diseases, e.g. various leukemias. When the patient is suffering from non-malignant diseases, e.g. various anemias, sublethal conditioning is used. Thus, when TBI is carried out, the patient is irradiated with a single or fractionated dose within the range of 7–16 Gy, preferably 7–10 Gy, most preferably 8 Gy, when lethal or supralethal irradiation is desired, and with a single or fractionated dose within the range of 3–7 Gy, preferably 6.5 Gy, when sublethal irradiation is desired. The fractionated dose may be administered during 1 to 7 days, once or 2–10 times daily.

Any immunosuppressive agent used in transplantation to control the rejection, or a combination of such agents, can be used according to the invention, such as prednisone, methyl prednisolone, azathioprine, cyclophosphamide, cyclosporine, monoclonal antibodies against T-cells, e.g. OKT3, and antisera to human lymphocytes (antilymphocyte globulin—ALS) or to thymus cells (antithymocyte globulin—ATG). Examples of myeloablative agents that can be used according to the invention are busulphan, dimethyl myleran and thiotepa.

In a preferred embodiment of the invention, the patients are treated with a combination of ATG, thiotepa and cyclophosphamide, after TBI.

The HLA-nonmatched donor may be an unrelated person to the family, but preferably will be a very close relative, most preferably a family member of the patient, such as one of the parents, a brother or a sister of the patient.

Bone marrow from the donor is obtained by aspiration of marrow from the iliac crest. T-cell depletion of bone marrow may be carried out by any known technique, for example, by soybean agglutination and E-rosetting with sheep red blood cells as described (Reisner et al., 1981, 1986).

Peripheral blood stem cells are obtained after stimulation of the donor with a single or several doses of a suitable cytokine, such as granulocyte colony-stimulating factor (G-CSF), granulocyte/macrophage colong-stimulating factor (GM-CSF) and interleukin-3 (IL-3). In a preferred embodiment of the invention, the donor is stimulated with G-CSF (Caspar et al., 1993).

In order to harvest desirable amounts of stem cells from the peripheral blood cells, leukapheresis is performed by conventional techniques (Caspar et al., 1993) and the final product is tested for mononuclear cells. T-cell depletion is carried out as for bone marrow and the final product is filtered and irradiated (15–40 Gy) before infusion.

The total dose of T-cell-depleted stem cells from bone marrow and peripheral blood that is to be administered according to the invention is at least 3-fold greater than conventional doses used in T-cell-depleted bone marrow transplantation. These conventional doses are within the range of $5 \times 10^8$–$3 \times 10^9$ T-cell-depleted bone marrow cells. According to the invention, when T cell depletion is carried out by soybean agglutination and E-rosetting with sheep red blood cells, the range of mononuclear cells (MNC) in bone marrow is between of $0.1$–$0.5 \times 10^8$/kg recipient, comprising an average of about $1.9 \times 10^6$/kg recipient of CD34+ stem cells. Still according to the invention, the total number of CD34+ stem cells that is to be administered to the patient is increased up to at least about 3 times the above amount of CD34+ cells in the T cell-depleted bone marrow. i.e. at least about $5.5 \times 10^6$/kg CD34+ cells. This can be achieved, for example, by the addition of T-cell-depleted stem cell-enriched peripheral blood cells to the T cell-depleted bone marrow cells, or by transplantation only of T cell-depleted stem cell-enriched peripheral blood cells in the desired high dose. The mobilization of the peripheral blood stem cells is done, for example, by stimulation of the donor with a suitable drug, e.g. a cytokine.

The method of the invention is suitable for the treatment of diseases curable by bone marrow transplantation, including leukemias, such as acute lymphoblastic leukemia (ALL), acute nonlymphoblastic leukemia (ANLL), acute myelocytic leukemia (AML) and chronic myelocytic leukemia (CML), severe combined immunodeficiency syndromes (SCID), osteopetrosis, aplastic anemia, Gaucher's disease, thalassemia and other congenital or genetically-determined hematopoietic abnormalities. In addition it can be used for BMT prior to the transplantation of an organ, e.g. kidney, from the same donor to the same recipient.

The invention will now be illustrated by the following non-limiting examples.

EXAMPLE 1

Engraftment of T Cell-depleted Haploidentical "Three Loci" Incompatible Transplants in Leukemia Patients Patients Seventeen patients (15 male, 2 female), median age 23.2 years (range 6–51), with advanced chemoresistant leukemia (5 AML, 9 ALL, 3 CML in blastic phase) were transplanted during a period of about 9 months. All patients received grafts from HLA haploidentical "three loci" incompatible (or mismatched) family members. 6 donors were siblings, 11 were parents. Anti-donor lymphocyte antibodies, as assayed in a complement-dependent microcytotoxicity crossmatch test were not detected in any of the 12 evaluated cases. The aforementioned is summarized in Table I below which sets forth the patient's characteristics and donor-host relationship.

TABLE I

Patient's characteristics and Donor-Host relationship

| UPN | Age/Sex | Disease | Status | Age/Sex | Relationship | HLA-ANALYSIS Donor | Host |
|---|---|---|---|---|---|---|---|
| 306 | 22/M | AML | REL | 45/M | Father | A2B35DR4 A11B7DR2 | A2B35DR4 A26B49DR6 |
| 313 | 37/M | AML | REL | 67/F | Mother | A2B35DR11 A30B7DR2 | A2B35DR11 A1B8DR3 |
| 315 | 17/M | ALL | REL | 40/F | Mother | A2B44DR17 BLB8DR4 | A2B44DR17 A2B18DR4 |
| 317 | 31/F | ALL | REL | 39/M | Brother | A24B18DR2 A2BLDR5 | A24B18DR2 A11BLDR7 |
| 319 | 15/M | CML | BT | 49/F | Mother | A2B35DR3 A3B58DR11 | A2B35DR3 A29B44DR7 |
| 320 | 22/M | CML | BT | 44/F | Mother | A24B19DR6 A2BLDR11 | A24B19DR6 A29B44DR1 |
| 321 | 2/M | AML | REL | 30/M | Brother | A2B51DR11 BLB16DR2 | A2B51DR11 BLB37DR4 |
| 329 | 6/M | ALL | REL | 33/M | Father | A1B35DR6 A32B18DQ1 | A1B35DR6 A30B38DR3 |
| 331 | 27/M | CML | BT | 45/F | Mother | A1B38DR7 A2B40DR2 | A1B38DR7 A29B44DR5 |
| 333 | 23/M | ALL | REL | 19/M | Brother | A26B39DR1 A2B8DR8 | A26B39DR1 A3B35DR10 |
| 334 | 51/F | ALL | REL | 55/F | Sister | A1B44 A26B7 | A1B44 A2B35 |
| 401 | 14/M | AML | REL | 44/M | Father | A2B18DR11 A3B51 | A2B18DR11 BLB17DR2 |

TABLE I-continued

Patient's characteristics and Donor-Host relationship

| UPN | Age/Sex | Disease | Status | Age/Sex | Relationship | HLA-ANALYSIS Donor | Host |
|---|---|---|---|---|---|---|---|
| 402 | 29/M | AML | REL | 30/M | Brother | A33B12DR7 A30B14DR3 | A33B18DR7 A24B14DR1 |
| 404 | 34/M | ALL | REL | 30/M | Brother | A1B7DR4 A31B35DR1 | A1B7DR4 A32B51 |
| 407 | 13/M | ALL | REL | 40/M | Father | A10B14 A2B51 | A10B14 A9B35 |
| 408 | 13/M | ALL | REL | 40/M | Father | A10B16 A9B18 | A10B16 A28B52 |
| 409 | 13/M | ALL | REL | 42/M | Father | A11B5DR12 A2B12DR13 | A11B5DR12 A9B15DR1 |

In Table I above the meanings of the various abbreviations are :
AML = acute myeloid leukemia
ALL = acute lymphoblastic leukemia
BT = blastic transformation
REL = relapse
BL = blank
M = male
F = female Conditioning Regimen All patients received 8 Gy total body irradiation (TBI) in a single dose at a fast dose rate 16 cGy/min midplane) from a 18 MV photon beam linear accelerator on day −5 (5 days prior to engraftment/transplant). Lungs were shielded by individual lead moulds; the corrected mean total lung dose was 7 Gy. Thiotepa (Lederle Laboratories, Pearl River, N.Y.) was administered i.v. on day −4 (4 days prior to engraftment) in two divided doses, 5 mg/kg body weight per dose (4 hours for each infusion, total dose 10 mg/kg body weight). On each day from days −4 to −1 (4 to 1 days prior to engraftment/transplant) rabbit anti-human thymocyte globin (ATG; Fresenius, AG Germany) at a dose of 5 mg/kg body weight was infused over 8 hours, followed by cyclophosphamide (Endoxin-Asta, Asta-Werke, Bielefeld, Germany) administered on days −3 and −2 (3 and 2 days prior to engraftment/transplant) at a dose of 60 mg/kg body weight. No immunosuppressive therapy was given as GvHD prophylaxis following transplant.

On day 0 (i.e. 5 days following the irradiation treatment), bone marrow from a HLA-nonmatched family member, depleted of T-cells by soybean agglutinin and E-rosetting was transplanted into each patient, and preparations of T-cell depleted peripheral blood mononuclear cells (PBMC) from the same donor were administered on days +1 and +2 (i.e. 1 and 2 days after bone marrow transplants; for preparation of the bone marrow and PBMC, see below).

Supportive Care

Patients were cared for in laminar air-flow rooms until the neutrophil count recovered to about $1 \times 10^9$/L (at least 0.5× $10^9$/L). All patients received prophylactic trimethoprim-sulfamethoxazole for Pneumocystis carinii, ciprofloxacin for selective gut decontamination, fluconazole for fungal prophylaxis, immunoglobulin (0.5 gr/kg weekly from day −5 to day +90) and total parenteral nutrition. Fever during the period of neutropenia was treated with broad spectrum antibiotics; amphotericin B was added if fever persisted. CMV-prophylaxis consisted of ganciclovir (10 mg/kg/day from day −6 to day −2 and resumed at 5 mg/kg/day from day +7 to day +21 followed by maintenance treatment with 5/mg/kg thrice weekly until day +90). Foscarnet (90 mg/kg/ day) was given from day −1 to day +10. All but one patient (UPN 306) received G-CSF (5 mg/kg/day) for a mean of 4.7 days (range 2–9) in the immediate post-transplant phase.

All blood products were filtered and irradiated before infusion.

Engraftment and Immunological Studies

Time to engraftment was assessed by determining the day after transplant on which patients achieved neutrophil count of $0.5 \times 10^9$/L and a platelet count of $2.5 \times 10^9$/L independent of transfusion support. Chimerism was assessed by karyotyping of peripheral blood lymphocytes and the analysis of restriction fragment length polymorphism (RFLP) in both peripheral blood and bone marrow (Yam, P. Y. et al., 1987). The degree of acute GVHD was assessed using standard clinical criteria (Glucksberg, H. et al., 1974).

Post-transplant lymphoid cell subsets were identified by two-color immunofluorescence and flowcytometry (Velardi, A. et al., 1988a). Cytotoxicity against a panel of NK cell-sensitive and resistant targets was evaluated by a 51-Cr release assay as described (Velardi, A. et al., 1990). T cell proliferation was assessed by stimulating cells with anti-CD3 MoAb, and pulsing the cultures with 3H-thymidine for 12 hours at the end of a 72-hour culture period. For detection of IL-2 activity in culture supernatants, the CTLL murine cell line assay was utilized (Velardi, A. et al., 1988b).

Bone Marrow and Peripheral Blood Mononuclear Cells Collection

Donor bone marrow cells were obtained under general anesthesia by multiple aspirations from the iliac crests bilaterally and cryopreserved, as discussed below. Recombinant human G-CSF (rhG-CSF; 12 ug/kg/day) was administered to donors by continuous subcutaneous infusion from 24 hours after bone marrow harvesting and continued for 5–7 days. Two to four leukaphereses were performed between days 4 and 7 in the first 7 donors, who received rhG-CSF for 6–7 days; while the remaining 10 donors, who were treated with rhG-CSF for 5–6 days, underwent two-three leukaphereses (days 4, 5 and 6).

The donors reported no untoward effects during or following the administration of rhG-CSF or from the blood collections.

Bone Marrow and Peripheral Blood Mononuclear Cell Processing

All bone marrow preparations were depleted of T lymphocytes using the soybean agglutination and E-rosetting technique, as previously described (Reisner, Y. et al., 1986). This procedure results in a 3–3.5 $\log_{10}$ reduction in the number of clonable T lymphocytes. Depletion of T lymphocytes from the peripheral blood mononuclear cells in the first seven cases, was achieved by a two step E-rosetting procedure, whereas the combined soybean agglutination and E-rosetting technique was used in the last ten cases. Aliquots were taken for differential cell counts, monoclonal antibody (MoAb) staining and GFU-GM assay at each stage of processing. T cell-depleted marrow and peripheral blood cells were frozen in a controlled rate liquid nitrogen freezer and stored in the vapor phase of liquid nitrogen. In some cases, the collections from peripheral blood were performed on the day before and on the day of the transplant; these cells were not cryopreserved.

CFU-GM were measured in whole blood and in the leukapheresis product by plating $0.5 \times 10^5$ mononuclear cells in a 3% agar solution containing 10% of 5637 cell-line conditioned medium, 20% fetal bovine serum and Iscove medium. Colonies of greater than 40 cells were counted on an inverted microscope (Leica, Wetzlar, Germany) after 10–14 days.

The number of CD34+ cells were measured both in whole blood and in the leukapheresis product with a direct immunofluorescence technique using the fluorescein conjugate HPCA-2 monoclonal antibody (Becton Dickinson, Palo Alto, Calif.). Negative control was assessed using a mouse IgG1-FITC. Cells were analyzed on a Profile II (Coulter Corporation, Hialeah, Fla.). A gate was established to include only lymphocytes and mononuclear cells. 10,000 cells were evaluated.

The T lymphocytes before and after T cell-depletion were evaluated with an immunocytological technique using an anti-CD3 monoclonal antibody as previously described (Cordell, J. L. et al., 1984).

RESULTS

Mobilization and Collection of Peripheral Blood Progenitor Cells (PBPC)

In the normal donors, under steady state hematopoiesis (baseline), minimal amounts of circulating CD34+ cells (median 0.5/uL blood; range 0 to 15/uL) and CFU-GM (median 122,7/ml; range 0 to 268) were detectable. With G-CSF treatment donor white cell count rose from a median of $6.7 \times 10^9$/L to $72 \times 10^9$/L by day 7.

Peak levels of CD34+ cells, as well as CFU-GM, were reached simultaneously at a median of 5 days. Median values of peak levels were 830.7 CD34+ cell/ul (range 92.8–1,035) and 12,347 CFU-GM/ml (range 549–20,126).

The 2–4 leukapheresis procedures yielded a mean total number of $10.4 \times 10^8$ mononuclear cells per kilogram donor body weight (range $4$–$23 \times 10^8$). The combined leukapheresis products contained a mean of $11.62 \pm 4.74 \times 10^6$/kg CD34+ cells (range 5.47–18.99) and $73.182 \pm 40.8 \times 10^4$/kg CFU-GM (range 13–132.53).

T Cell-depletion of Bone Marrow and Peripheral Blood Mononuclear Cells

Table II lists the mean number (kg/body weight) of mononuclear cells, CFU-GM, CD34+ and CD3+ cells present in bone marrow, peripheral blood and the combined products given to the patients following T cell-depletion.

The median dose of T cells infused was higher in the first seven patients (group I) who received E-rosette-depleted peripheral blood mononuclear cells (PBMC) than in those (group II) whose leukapheresis product was depleted of T lymphocytes by the combined soybean agglutination (SBA) and E-rosetting technique. In both groups the average concentration of CFU-GM in the combined product was 7–10 fold greater than that found in bone marrow alone.

TABLE II

Characteristics of Transplanted Bone Marrow and Peripheral Blood Cells after T Cell-Depletion

| | GROUP I | | | GROUP II | | |
|---|---|---|---|---|---|---|
| | BM | PBMC | TOTAL | BM | PBMC | TOTAL |
| MNC ($\times 10^8$/kg)[a] | 0.31 | 5.96 | 6.27 | 0.27 | 2.98 | 3.25 |
| CFU-GM($\times 10^4$/kg) | 12.77 | 71.55 | 84.32 | 4.56 | 35.80 | 40.36 |
| CD34+ ($\times 10^6$/kg) | 1.9 | 12 | 13.9 | N.D. | 16 | 16 |
| CD3+ ($\times 10^5$/kg) | 0.32 | 5.91 | 6.23 | 0.19 | 1.24 | 1.43 |

[a]recipient body weight
Group 1 = 7 donors. BM was T cell-depleted by SBA and 1 step E-rosette. PBMC were T cell-depleted by only 2 step E-rosette. Donors underwent 2–4 leukaphereses.
Group II = 10 donors. BM and PBMC were T cell-depleted by SBA + 2 step E-rosette. Donors underwent 2–3 leukaphereses.

Engraftment

One patient (UPN331) rejected the graft on the 18th post-transplant day, after initial myeloid engraftment. RFLP analysis of granulocytes confirmed that they were donor-derived on day 14 (data not shown). This early rejection was associated with the abrupt emergence of host T cells that exhibited donor specific cytotoxic reactivity.

The other 16 patients had early and sustained engraftment. They achieved peripheral blood neutrophil counts over $0.5 \times 10^9$/L and over $1.0 \times 10^9$/L at a mean of 10.2 days (range 9–17) and 11.5 days (range 10–22), respectively. Platelet counts of $25 \times 10^9$/L and $50 \times 10^9$/L were reached at a mean of 17.2 days (range 10–29) and 30 days (range 14–60), respectively. The time course of engraftment is illustrated in FIG. 1. The curves represent the time required for T cell-depleted "three loci" incompatible transplants according to the present invention, to reach 0.5 and $1.0 \times 10^9$/neutrophils/L, as compared with our own historical control group of 23 patients who received autologous chemotherapy/cytokine-mobilized PBPCs (data not shown) and 93 patients transplanted with T cell-depleted HLA genotypically identical bone marrows (data not shown). From this comparison it was observed that the T cell-depleted incompatible transplants of the present invention enabled a more rapid obtention of these amounts of neutrophils in essentially all of the patients examined.

RFLP analysis documented full donor type chimerism in both peripheral blood and bone marrow of the 16 engrafted patients (data not shown).

Immune Reconstitution

Phenotypic and functional analyses of post-transplant lymphocyte subsets were performed and compared with those obtained in HLA-matched T cell-depleted BMT recipients (data not shown). Whereas essentially identical data were obtained for B-cell and T-cell subsets in the two BMT settings, a two-fold increase in the early (1–2 months post-grafting) natural killer cell wave was noted in mismatched, i.e. the present invention, as compared to matched, transplants. The number of CD56+/CD16+/CD3−, NK cells reached a peak value of 707±212 ul after mismatched BMT and 306±19 after matched BMT.

Graft Versus Host Disease

One patient (UPN317) developed grade IV acute GVHD which was fatal. It is worth noting that she received a greater quantity of T lymphocytes ($11.30 \times 10^5$/kg) than any of the other patients. There were no other cases of acute GVHD≧grade II.

Toxicity and Clinical Outcome

In almost all patients, thiotepa caused a sunburn-like erythema, that gradually faded and peeled-off; mild reversible oral mucositis developed in all patients. Mild diarrhea was generally seen within 2–4 days of completion of the conditioning regimen and resolved spontaneously. Transient hemorrhagic cystitis complicated the course of four patients and resolved with hydratation and continuous bladder irrigation. Moderate veno occlusive disease (VOD) of the liver occurred in two patients; their bilirubin levels ranged from 2 to 7 mg/dl and returned to normal in ten days with sodium restriction and diuretics. The median time to onset of VOD was 6 days post-transplant.

Six patients developed interstitial pneumonitis between days +14 and +160 and died from respiratory failure (Table III). No infectious cause could be identified in two (UPN319, 404), while CMV was the causative agent in four (UPN315, 320, 321, 334). Hematological remission and full donor type chimerism was documented in all 6 cases at the time of death. CMV-related gastroenteritis occurred in 5 patients but resolved with ganciclovir treatment.

The one patient (UPN331) who experienced graft failure and the one patient with GVHD, died. One (UPN 401) died from fungal infection. There have been two relapses, both in patients transplanted for ALL, within 2 months from the transplant..

Six patients are alive and well at a median follow-up of 230 days (range 100–485) post-transplant, all with a Karnofsky performance status of 100%.

The above clinical outcome of the present study is summarized in Table III.

TABLE III

| | | Clinical Outcome | | | |
|---|---|---|---|---|---|
| UPN | Disease | Status at transplant | Blasts (%) in bone marrow | Engraftment | A-GvHD (grade) | Current Status (June 30, 1994) |
| 306 | AML | 2nd Relapse | 80 | YES | 0 | Alive in CCR on Day +485 |
| 313 | AML | Induction Failure | 100 | YES | 0 | Alive in CCR on Day +413 |
| 315 | ALL | 3rd Relapse | 100 | YES | 0 | Died on Day 120 from CMV-IP |
| 317 | ALL | 2nd Relapse | 100 | YES | IV | Died on Day 60 from GvHD |
| 319 | CML | 2nd Blast crisis | 80 | YES | 0 | Died on Day 90 from Idiopat-IP |
| 320 | CML | 3rd Blast crisis | 16 | YES | 0 | Died on Day 20 from CMV-IP |
| 321 | AML | 3rd Relapse | 100 | YES | 0 | Died on Day 18 from CMV-IP |
| 329 | ALL | 3rd Relapse | 100 | YES | 0 | Relapsed on Day 60, Died on Day 70 |
| 331 | CML | 2nd Blast crisis | 30 | NO | N.E. | Died on Day 45 from sepsis |
| 333 | ALL | 3rd Relapse | 15 | YES | 0 | Relapsed on Day 50, Died on Day 60 |
| 334 | ALL | 2nd Relapse | 15 | YES | I | Died on Day 180 from Idiopat-IP |
| 401 | AML | 3rd Relapse | 100 | YES | 0 | Died on Day 45 from sepsis |
| 402 | AML | Induction Failure | 100 | YES | I | Alive in CCR on Day +157 |
| 404 | ALL | 2nd Relapse | 100 | YES | 0 | Died on Day 62 from Idiopat-IP |
| 407 | ALL | 2nd Relapse | 15 | YES | I | Alive in CCR on Day +126 |
| 408 | ALL | 3rd Relapse | 15 | YES | I | Alive in CCR at Day +110 |
| 409 | ALL | 3rd Relapse | 10 | YES | I | Alive in CCR on Day +100 |

The abbreviations in Table III above are the same as in Table I, with the following additions :
N.E. = Not Evaluable
CCR = Continuous Complete Remission
IP = Interstitial pneumonitis Thus, in our study a 7–10 fold increase in the dose of the transplant inoculum was achieved by adding T cell-depleted rhG-CSF mobilized PBPCs to the T cell-depleted bone marrow.

The very large cell dose we infused after the intensive conditioning regimen were followed by prompt and sustained engraftment in 16 of 17 recipients of haploidentical "three loci" mismatched T cell-depleted bone marrow. Neutrophil and platelet recovery was very rapid and the engraftment characteristics were very similar to those observed in syngeneic PBMC transplants or in our historical control group of patients who received autologous chemotherapy/rhG-CSF-mobilized PBPCs.

The impressive rate of engraftment across the most difficult histoincompatibility barrier demonstrate that in humans, as in mice, the stem cell dose plays a critical role in the engraftment of T cell-depleted transplants. This concept is further supported by the finding that the same pre-transplant conditioning failed to promote engraftment in any of the five patients transplanted with conventional doses of T cell-depleted "three loci" mismatched bone-marrows (our unpublished observations).

One potential major concern raised by the use of a large T cell-depleted inoculum is an increased risk of GVHD, mainly due to T cell contamination of PBPCs. However, greater than grade I GVHD was extremely rare and occurred in only one of the evaluable patients who received the largest number of T cells ($11.3 \times 10^5$/kg, almost two fold more than the average numbers administered to group I and about ten fold more than the average of group II), greater than $2 \times 10^5$/kg which is considered the threshold dose of clonable T cells which leads to GVHD. However, it is likely that ATG, given between days −5 and −2, contributes to lowering both the frequency and severity of GVHD by exerting a cytotoxic effect against donor inoculum T lymphocytes.

Of more concern is the question of CMV disease. CD8+ CMV-specific cytotoxic T lymphocytes (CTL) are responsible for protective immunity and elimination of active infection. As CMV-specific CTL responses may require an extended time period after mismatched BMT and they are HLA-restricted, susceptibility for CMV-infections is greater with mismatched than matched BMT. The rapid hematopoietic reconstitution observed in our series of patients, should permit early prophylaxis of CMV infections with ganciclovir and so contribute to lowering mortality. After the schedule of ganciclovir was modified to begin day +7, no case of CMV-pneumonia was documented in the 9 patients (see group II patients, Tables II and III).

EXAMPLE 2

Engraftment of T Cell-depleted Transplants in Sublethally Irradiated Recipients

In Example 1, the engraftment of the T cell-depleted bone marrow and PBMC transplants was studied in patients who had all received lethal doses of irradiation. Based on the encouraging (6 living, apparently healthy patients) results of this study, we extended this approach to determine whether in sub-lethally irradiated recipients engraftment of such bone marrow and PBMC transplants could also occur successfully, without the need for post-transplant immune suppression.

Using an accepted animal (mouse) model, we tested the feasibility of such an approach for human applications, according to the following treatment protocol:C3H/HeJ mice were conditioned by a single dose TBI in the range of 6–8 Gy and then transplanted with increasing doses of T-cell depleted bone marrow (BM) from C57BL/6 donors. Donor type chimerism determination one month post-transplant revealed that while engraftment was effective in mice conditioned with 8 Gy upon transplantation of $8 \times 10^6$ cells, it could also be generated following conditioning with a sublethal dose of 6.5 Gy TBI (survival in untransplanted mice>90%), provided that the BM dose was increased by about 4 fold. Thus, transplantation of $40 \times 10^6$, $20 \times 10^6$ and $10 \times 10^6$ cells led to donor type chimera in 18/21, 13/26 and 1/26 of the recipients, respectively.

Transplantation of T-cell depleted BM of C57BL/6-nude donors necessitated $200 \times 10^6$ cells to achieve engraftment, but repletion of the BM with $5 \times 10^4$ purified thymocytes (using peanut agglutinin, PNA) reduced the minimal number required to achieve donor type chimeras to $50 \times 10^6$ cells, similar to the results with normal C57BL/6 marrow.

These results suggest that the new source of G-CSF mobilized human hematopoietic pluripotential stem cells (see Example 1) which can provide at least one log more of such cells, compared to the bone marrow alone, may extend the use of mismatched bone marrow transplants to patients with non-malignant diseases for whom supralethal or lethal conditioning is not a prerequisite, and thus a sublethal conditioning is suitable. Examples of such diseases are SCID, osteopetrosis, aplastic anemia, Gaucher's disease, thalassemia and other congenital or genetically-determined hematopoietic abnormalities, or prior to transplantation of another organ from the same donor to a same recipient.

REFERENCES

1. Caspar, C. B., Seger, R. A., Burger, J. and Gmur, J. (1993). Effective stimulation of donors for granulocyte transfusions with recombinant methionyl granulocyte colony-stimulating factor. Blood 81:2866–71.

2. Cordell, J. L., Falini, B., Erber, W., Ghosh, A. K., Abdulaziz, Z., McDonald, S., Pulford, K. A. F., Stein, H. and Mason, D. Y. (1984). Immunoenzyme labeling of monoclonal antibodies using immune complexes of alkaline phosphatase and monoclonal anti-alkaline phosphatase (APAAP complexes). J. Histochem. Cytochem. 32:219.

3. Gale, R. P. and Reisner, Y. (1986). Graft rejection and graft-versus-host-disease:mirror images. Lancet 1:1468.

4. Gianni, A. M., Siena, S., Brengi, M., Boccadoro, M., Lombardi, F., Bengala, C., Bonadonna, G. and Pileri, A. (1990). Durable and complete hematopoietic reconstitution after autografting of rhGM-CSF exposed periperal blood progenitor cells. Bone Marrow Transplant. 6:143.

5. Glucksberg, H., Storb, R., Refer, A., Buckner, C. D., Neiman, P. E., Clift, R. A., Lerner, K. G. and Thomas, E. D. (1974). Clinical manifestations of graft-versus-host disease in human recipients of marrow from HLA-matched sibling donors. Transplantation. 18:295.

6. Lapidot, T., Terenzi, A., Singer, T. S., Salomon, O. and Reisner, Y. (1989). Enhancement by dimethyl myleran of donor type chimerism in murine recipients of bone marrow allografts. Blood 73:2025.

7. Matsunaga, T., Sakamaki, S., Kohgo, Y.,Ohi, S., Hirayama, Y. and Niitsu, Y. (1993). Recombinant human granulocyte colony-stimulating factor can mobilize sufficient amounts of peripheral blood stem cells in healthy volunteers for allogeneic transplantation. Bone Marrow Transplant 11:103.

8. Molineux, G., Pojda, Z., Hampson JN, Lord BI, Dexter, TM. (1990) Transplantation potential of peripheral blood stem cells induced by granulocyte colony-stimulating factor. Blood 76:2153.

9. O'Reilly, R. J., Collins, N. H., Kernan, N., Brochstein, J., Dinsmore, R., Kilpatrick, D., Siena, S., Keever, C., Shank, B., Wolf, L., Dupont, B. and Reisner, Y. (1985). Transplantation of marrow depleted of T-cells by soybean lectin agglutination and E-rosette depletion : major histocompatibility complex-related graft resistance in leukemia transplant recipients. Transplant Proc. 17:455.

10. O'Reilly, R. J., Kernan, N. A., Cunningham, I., Brochstein, J., Castro-Malaspina, H., Laver, J., Flomenberg, N., Emanuel, D., Gulati, S., Keever, C. A., Small, T. N., Collins, N. H., and Bordignon, C. (1988) Allogeneic transplants depleted of T cells by soybean lectin agglutination and E-rosette depletion. Bone Marrow Transplant. 3(1):3.

11. O'Reilly, R. J., Keever, C. A., Small, T. N. and Brochstein, J. (1989). The use of HLA non-identical T-cell-depleted marrow transplants for correction of severe combined immunodeficiency disease. Immunodefic. Rev. 1:273.

12. Reisner, Y., Itzicovitch, L., Meshorer, A. and Sharon, N. (1978). Hemopoietic stem cell transplantation using mouse bone-marrow and spleen cells fractionated by lectins. Proc. Natl. Acad. Sci. USA. 75;2933.

13. Reisner, Y., Kapoor, N., Kirkpatrick, D., Pollack, M. S., Dupont, B., Good, R. A. and O'Reilly, R. J. (b 19811 ). Transplantation for acute leukemia with HLA-A and B non-identical parental marrow cells fractionated with soybean agglutinin and sheep red blood cells. Lancet ii:327.

14. Reisner, Y., Kapoor, N., Good, R. A. and O'Reilly, R. J. (1984). Allogeneic bone marrow transplantation in mouse, monkey and man using lectin-separated grafts. In *Tolerance in Bone Marrow and Organ Transplantation*. Elsevier, Slavin, S. (ed.) p. 293.

15. Reisner, Y., Freidrich, W. and Fabian, I. (1986). A shorter procedure for preparation of E-rosette-depleted bone marrow for transplantation. Transplantation 42:312.

16. Reisner, Y. (1990). Engraftment of T-cell-depleted bone marrow in murine models for allogeneic bone marrow transplantation. In *Bone Marrow Transplantation*. Kluwer Academic Publishers. R. Champlin (ed.), p.9.

17. Russel, N. H., Hunter, H. Rogers, S., Hanley, J. and Anderson, D. (1993). Peripheral blood stem as an alternative to marrow for allogeneic transplantation. Lancet 0.341:1482.

18. Terenzi, A., Lubin I., Lapidot, T., Salomon O., Faktorowich Y., Rabi I., Martelli M. F. and Reisner Y. (1990). Enhancement of T-cell depleted bone marrow allografts in mice by thiotepa. Transplantation. 50:717.

19. Vallera, D. A. and Blazer, B. R. (1989). T-cell depletion for graft-versus-host disease (GVHD) prophylaxis:a perspective on engraftment in mice and humans. Transplantation 47:751.

20. Velardi, A., Cucciaiaoni, S., Terenzi, A., Aversa, F., Quinti, I., Grossi, C. E. Grignan, F. and Martelli, M. F. (1988a). Acquisition of immunoglobulin isotype diversity after bone marrow transplantation in adults. A recapitulation of normal B-cell ontogeny. J. Immunol. 141:815.

21. Velardi, A., Terenzi, A., Cucciaioni, S., Millo, R., Grossi, C. E., Grignani, F. and Martelli, M. F. (1988b) Imbalance within peripheral blood T-helper (CD4+) and T-suppressor (CD8+) cell populations in the reconstitution phase after human bone marrow transplantation. Blood. 71:1196.

22. Velardi, A., Varese, P., Pende, D., Grossi, C. E., Dembech, C., Albi, N., Terenzi, A., Moretta, L., Martelli, M. F. and Mingari, M. C. (1990). Cytolytic functions of clonable T cells after human bone marrow transplantation. Blood 75:1364.

23. Weaver, C. H. Buckner, C. D., Longin, K., Appelbaum, F. R., Rowley, S., Lileby, K., Miser, J., Storb, R., Hansen J. A. and Bensinger, W. (1993). Synergeneic transplantation with peripheral blood mononuclear cells collected after the administration of recombinant human granulocyte colony-stimulating factor: Blood. 82:1981.

24. Yam, P. Y., Petz, L. D., Knowlton, R. G., Wallace, R. B., Stock, A. D., deLange, G., Brown, V. A., Donis-Keller, H. and Blume, K. G. (1987). Use of DNA restriction fragment length polymorphisms to document marrow engraftment and mixed hematopoietic chimerism following bone marrow transplantation. Transplantation. 43:399.

We claim:

1. A method for transplantation to a human patient in need therefor which comprises:
   i) conditioning the human patient under sublethal, lethal or supralethal conditions; and
   ii) transplanting to the conditioned human patient an amount of T-cell-depleted stem cells such that at least about $5.5 \times 10^6$ CD34+ cells per kilogram body weight of the patient is transplanted.

2. The method according to claim 1, in which the T-cell-depleted stem cells comprise T-cell-depleted bone marrow cells and T-cell-depleted stem cell-enriched peripheral blood cells obtained from a HLA-nonmatched donor.

3. The method according to claim 2, in which the T-cell-depleted bone marrow cells are prepared from bone marrow and the T-cell-depleted stem cell-enriched peripheral blood cells are prepared from peripheral blood by treating the bone marrow and peripheral blood with soybean agglutinin and E-rosetting with sheep red blood cells.

4. The method according to claim 1, in which the T-cell-depleted stem cells are prepared from bone marrow and/or peripheral blood by treating the bone marrow and/or peripheral blood with soybean agglutinin and E-rosetting with sheep red blood cells.

5. The method according to claim 1, in which the T-cell-depleted stem cells are from a donor who is a close relative of the patient.

6. The method according to claim 1, in which the T-cell-depleted stem cells comprise T cell-depleted stem cell-enriched peripheral blood cells obtained by leukapheresis of peripheral blood from a donor after stimulation of the donor by a suitable cytokine.

7. The method according to claim 6, in which the donor is stimulated with granulocyte colony-stimulating factor (G-CSF).

8. The method according to claim 1, in which said lethal or supralethal conditions include total body irradiation (TBI).

9. The method according to claim 8, in which a single or fractionated irradiation dose within the range of 7–16 Gy TBI is used.

10. The method according to claim 9, in which the human patient receives a 8 Gy single dose TBI.

11. The method according to any one of claims 8 to 10, in which the human patient is conditioned by TBI followed by treatment with myeloablative and immunosuppressive agents.

12. The method according to claim 11, in which the myeloablative agent is selected from busulphan, dimethyl myleran and thiotepa, and the immunosuppressive agent is selected from prednisone, methyl prednisolone, azathioprine, cyclophosphamide, cyclosparine, monoclonal antibodies against T cells, antilymphocyte globulin and antithymocyte globulin.

13. The method according to claim 11, in which the myeloablative agent is thiotepa and the immunosuppressive agents are antithymocyte globulin and cyclophosphamide.

14. The method according to claim 1, in which the human patient is afflicted with a malignant disease.

15. The method according to claim 1, in which the human patient is afflicted with acute lymphoblastic leukemia (ALL), acute myelocytic leukemia (AML) or chronic myelocytic leukemia (CML).

16. The method according to claim 1, in which the T-cell-depleted stem cells comprise either (a) T-cell-depleted bone marrow cells and T-cell-depleted stem cell-enriched peripheral blood cells, or (b) T-cell-depleted stem cell-enriched peripheral blood cells.

17. The method according to any one of claims 1–7 or 16, in which said lethal or supralethal conditions include treatment with myeloablative and immunosuppressive agents without total body irradiation (TBI).

18. The method according to claim 17, in which the myeloablative drug busulphan is administered to the human patient from day –8 to day –5 prior to transplant at a daily dose of 2–5 mg per kilogram body weight of the human patient for lethal conditions and above 5 mg per kilogram body weight of the human patient for supralethal conditions, and this treatment is followed by administration of the immunosuppressive drug cyclophosphamide from day –4 to day –1 prior to transplant at a daily dose of 50 mg per kilogram body weight of the human patient.

19. The method according to claim 17, in which the myeloablative agent is selected from busulphan, dimethyl myleran and thiotepa, and the immunosuppressive agent is selected form prednisone, methyl prednisolone, azathioprine, cyclophosphamide, cyclosparine, monoclonal antibodies against T cells, antilymphocyte globulin and antithymocyte globulin.

20. The method according to any one of claims 1–9 or 16, in which the human patient is afflicted with a malignant or non-malignant disease.

21. The method according to any one of claims 1–7 or 16, in which said sublethal conditions include total body irradiation (TBI).

22. The method according to claim 21, in which a single or fractionated irradiation dose within the range of 3–7 Gy TBI is used.

23. The method according to claim 22, in which a single or fractionated dose of about 6.5 Gy TBI is used.

24. The method according to claim 21, in which the human patient is conditioned by TBI followed by treatment with myeloablative and immunosuppressive agents.

25. The method according to claim 24, in which the myeloablative agent is selected form busulphan, dimethyl myleran and thiotepa, and the immunosuppressive agent is selected form prednisone, methyl prednisolone, azathioprine, cyclophosphamide, cyclosparine, monoclonal antibodies against T cells, antilymphocyte globulin and antithymocyte globulin.

26. The method according to claim 25, in which the myeloablative drug busulphan is administer to the patient from day –8 to day –5 prior to transplant at a daily dose of 1–2 mg per kilogram body weight of the human patient, and this treatment is followed by administration of the immunosuppressive drug cyclophosphamide from day –4 to day –1 prior to transplant at a daily dose of 50 mg per kilogram body weight of the human patient.

27. The method according to any one of claims 1-7 or 16, in which the human patient is afflicted with a non-malignant disease.

28. The method according to claim 27, in which the human patient is afflicted with aplastic anemia, osteopetrosis, severe combined immunodeficiency syndromes (SCID), Gaucher's disease, thalassemia or a congenital or genetically-determined hematopoietic abnormality, or the patient is to receive a bone marrow transplant prior to receipt of an organ transplant, wherein the bone marrow and the organ are from the same donor.

29. The method according to claim 20, in which said sublethal conditions include treatment with myeloablative and immunosuppressive agents without TBI.

30. The method according to claim 29, in which the myeloablative drug busulphan is administered to the human patient from day –8 to day –5 prior to transplant at a daily dose of 1–2 mg per kilogram body weight of the human patient, and this treatment is followed by administration of the immunosuppressive drug cyclophosphamide from day –4 to day –1 prior to transplant at a daily dose of 50 mg per kilogram body weight of the human patient.

31. The method according to claim 29, in which the myeloablative agent is selected from busulphan, dimethyl myleran and thiotepa, and the immunosuppressive agent is selected form prednisone, methyl prednisolone, azathioprine, cyclophosphamide, cyclosparine, monoclonal antibodies against T cells, antilymphocyte globulin and antithymocyte globulin.

32. A method for treatment of a human leukemia patient which comprises:
  i) conditioning the human leukemia patient under lethal or supralethal conditions with total body irradiation (TBI), antithymocyte globulin (ATG), thiotepa and cyclophosphamide; and
  ii) transplanting to the conditioned human leukemia patient an average of about $0.31 \times 10^8$ T-cell-depleted bone marrow cells per kilogram body weight of the human leukemia patient and an average of about $6 \times 10^8$ T-cell-depleted peripheral blood cells per kilogram body weight of the human leukemia patient, wherein the T-cell-depleted bone marrow cells and the T-cell-depleted peripheral blood cells are from a HLA-nonmatched family member who was prior stimulated with granulocyte colony-stimulating factor (G-CSF).

* * * * *